United States Patent
Fay et al.

[11] Patent Number: 6,149,691
[45] Date of Patent: Nov. 21, 2000

[54] SELF-INFLATING SOCKET HAVING ENCASED GEL

[76] Inventors: John N. Fay; Cheryl A. Fay, both of 1120 Boca Ciega Isle, St. Pete Beach, Fla. 33706

[21] Appl. No.: 09/106,057

[22] Filed: Jun. 26, 1998

[51] Int. Cl.[7] ........................................ A61F 2/80
[52] U.S. Cl. ................................... 623/37; 623/33
[58] Field of Search .................. 623/32, 34–37, 623/33

[56] References Cited

U.S. PATENT DOCUMENTS

| | | | |
|---|---|---|---|
| 3,309,714 | 3/1967 | Porten | 623/37 |
| 5,735,906 | 4/1998 | Caspers | 623/34 |
| 5,830,237 | 11/1998 | Kania | 623/37 |

FOREIGN PATENT DOCUMENTS

| | | | |
|---|---|---|---|
| 2 620 933 A1 | 3/1989 | France | 623/36 |
| 25 40 138 A1 | 3/1977 | Germany | 623/37 |
| 1337080 | 9/1987 | U.S.S.R. | 623/35 |
| 1739990 A1 | 6/1992 | U.S.S.R. | 623/36 |

*Primary Examiner*—David H. Willse
*Attorney, Agent, or Firm*—Ronald E. Smith; Smith & Hopen, P.A.

[57] ABSTRACT

A socket has a gelatinous core to provide an enhanced cushioning effect for a residual limb. The gelatinous material is covered by a flexible inner cover that shields the skin of the residual limb from the gel and by a flexible outer cover that shields the inner wall of a prosthetic frame from the gel. The inner cover prevents the gel from absorbing body oils and therefore eliminates odors associated with liners formed of gelatinous materials. A self-inflating foam pad is positioned between the inner and outer covers to adjust the fit as needed when the residual limb changes in volume. The pad initially has substantially no air in its interstitial spaces and air is admitted when the patient opens a valve. This prevents over-pressurization of the pad because the maximum pressure that can be exerted by the pad is determined by the prosthetist when the patient is fitted with a prosthesis.

14 Claims, 5 Drawing Sheets

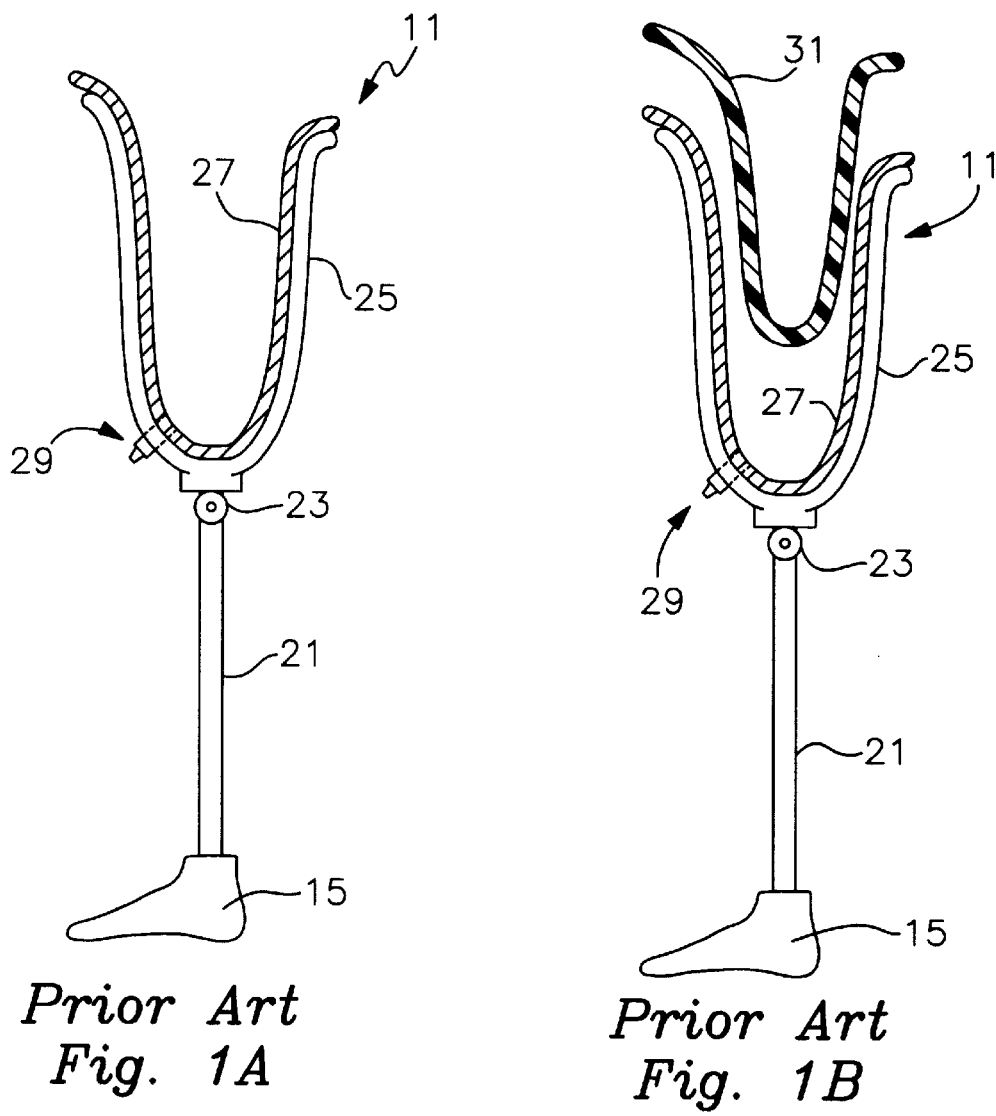
Prior Art
Fig. 1A
Prior Art
Fig. 1B

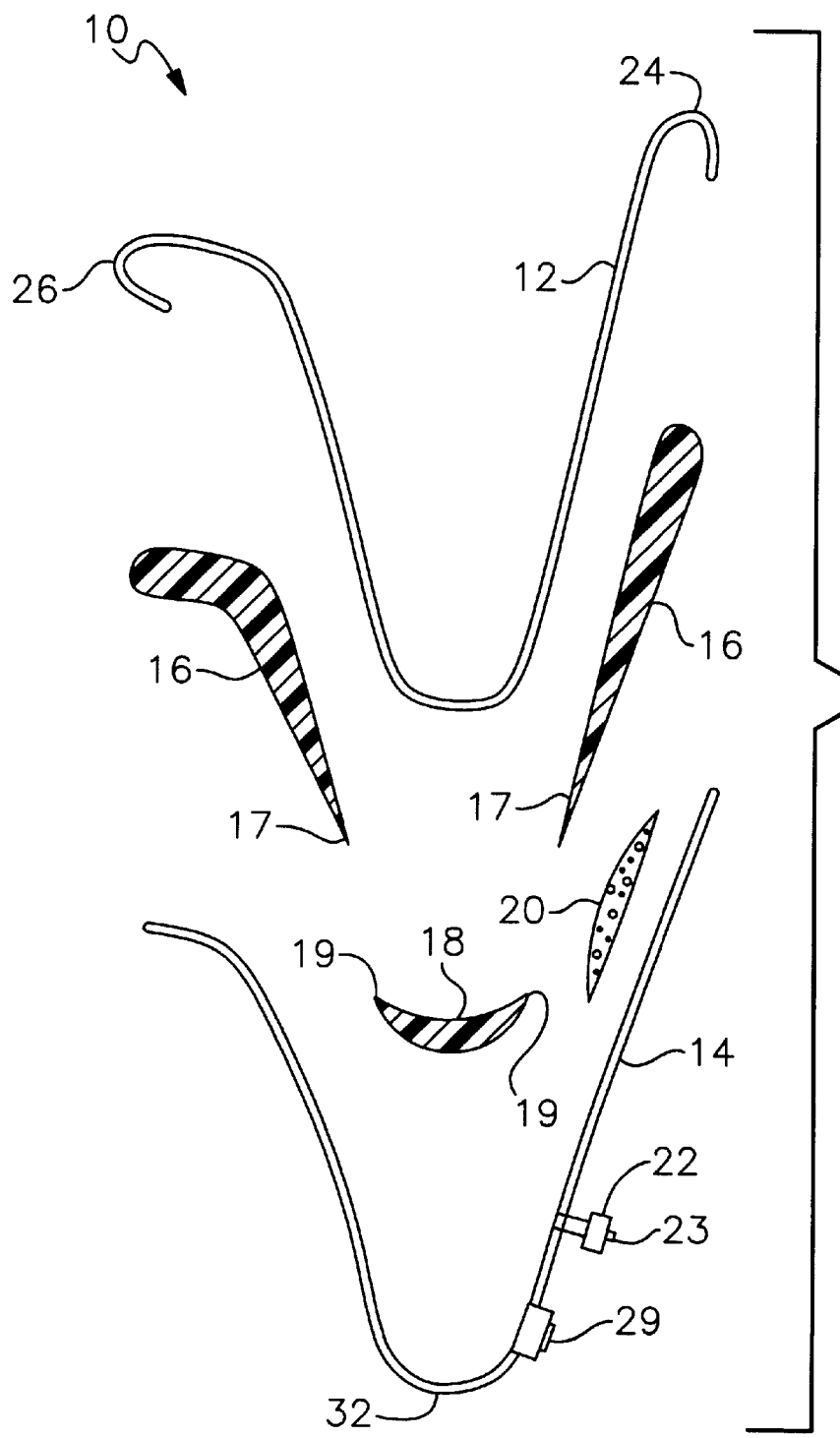
Fig. 2

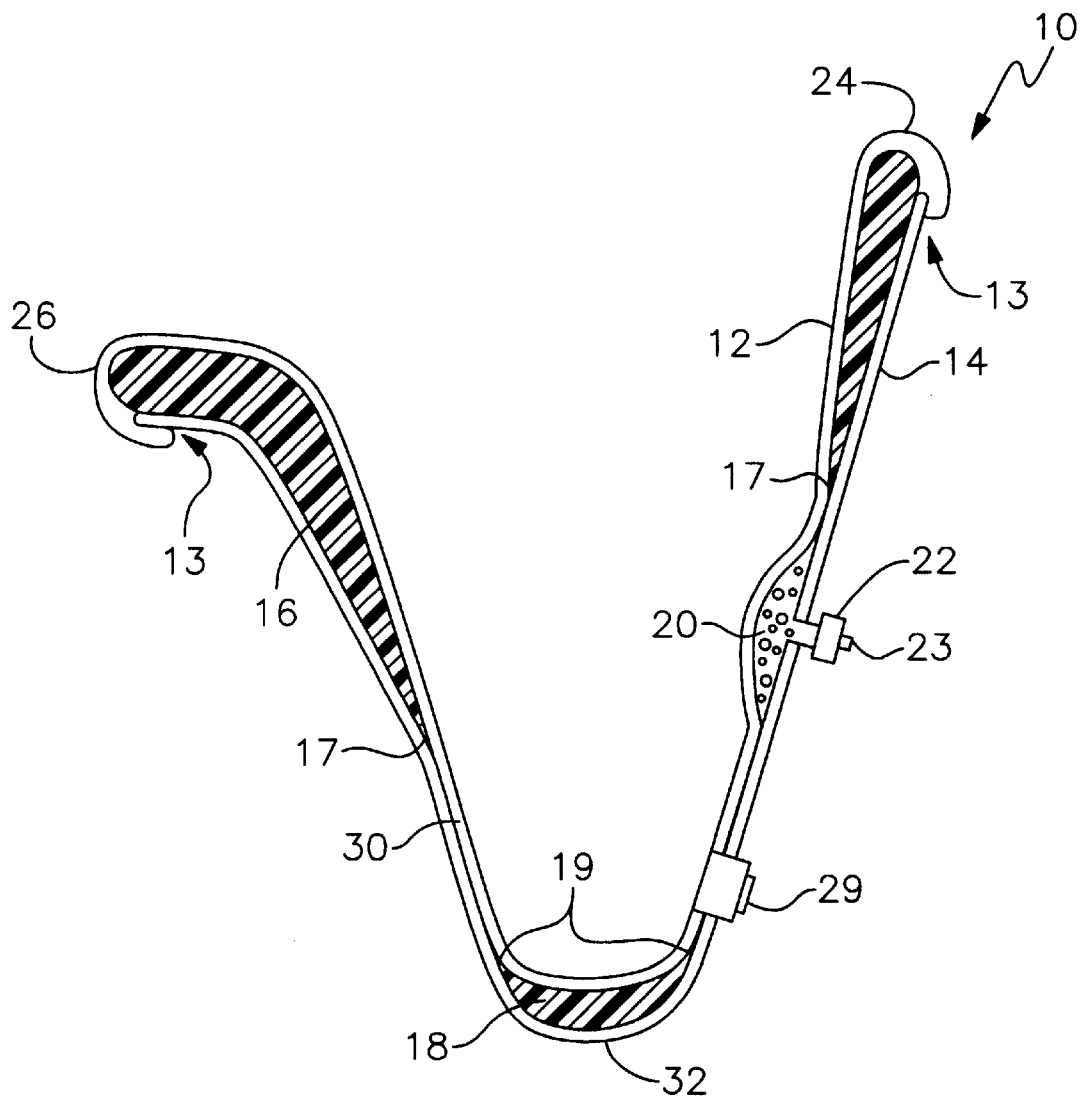
Fig. 3

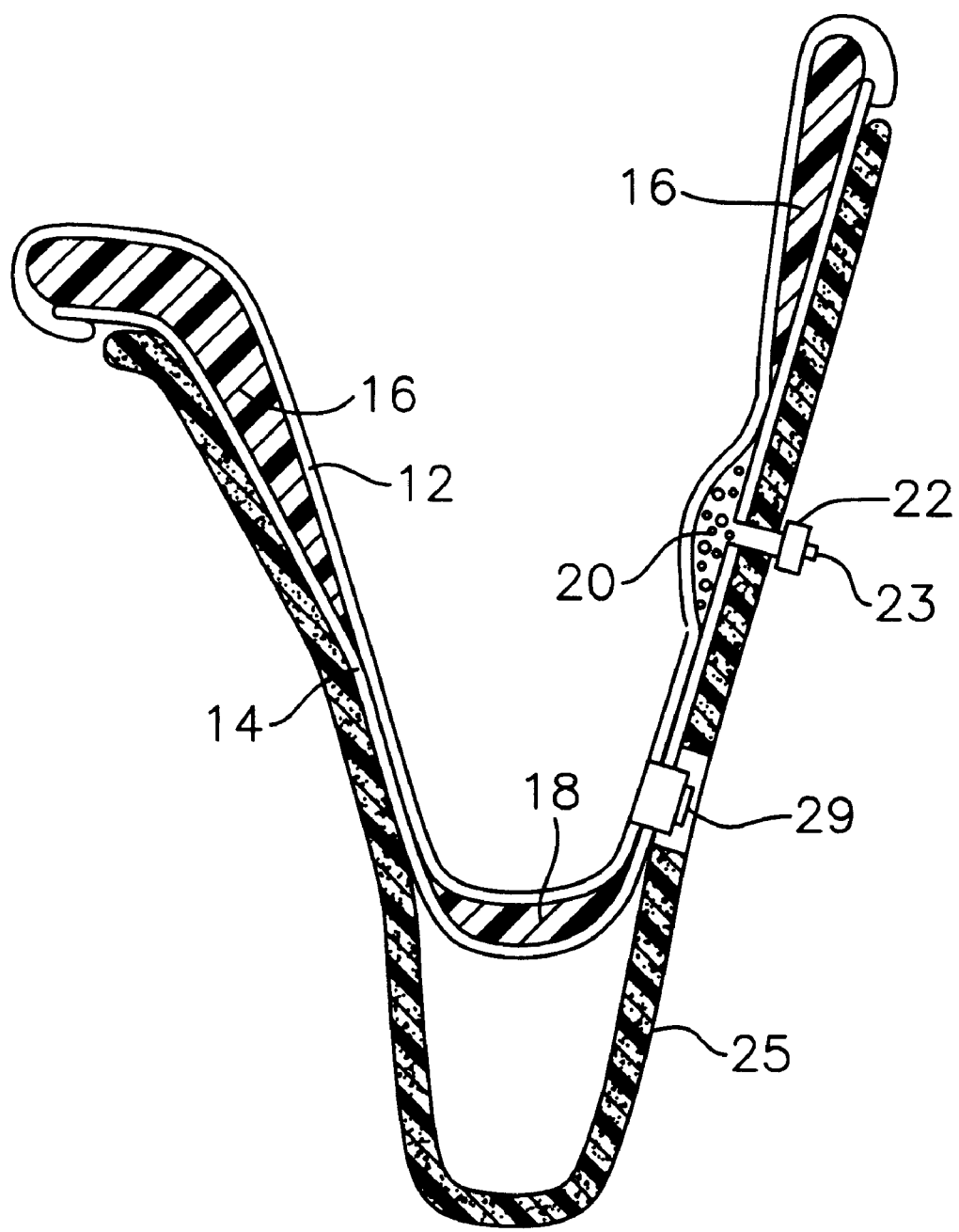
Fig. 4

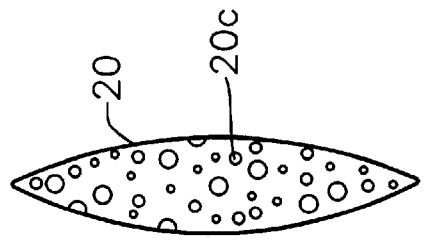
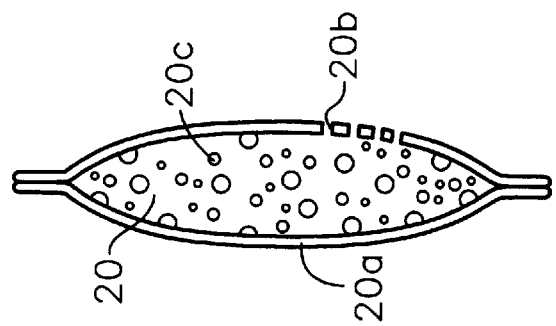
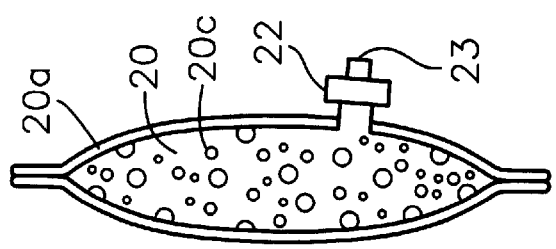
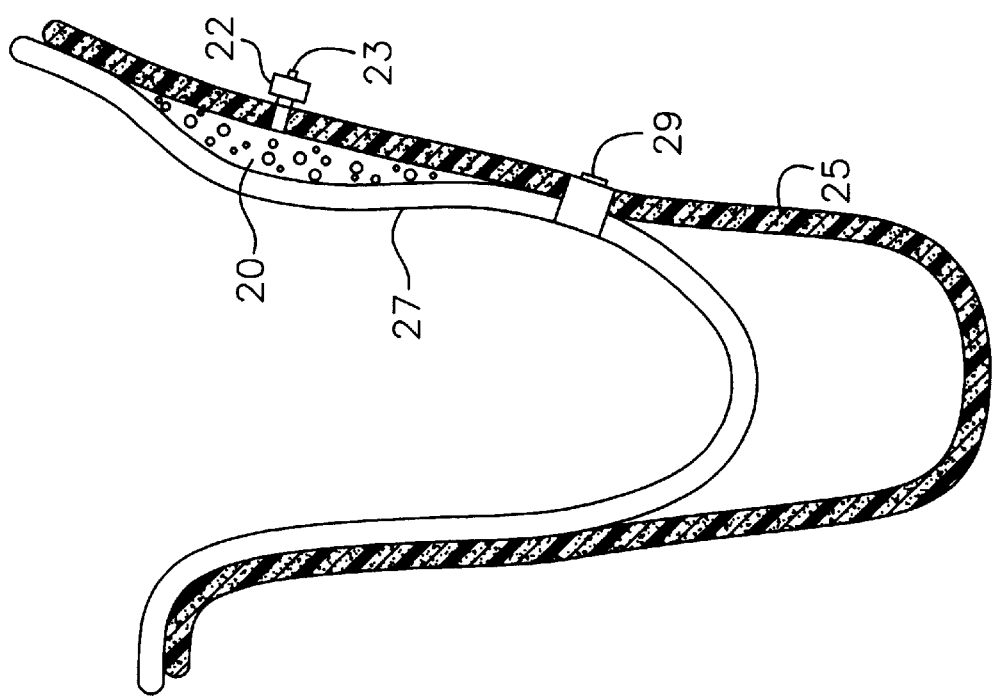

SELF-INFLATING SOCKET HAVING ENCASED GEL

BACKGROUND OF THE INVENTION

1. Field of the Invention

This invention relates, generally, to prosthetic devices. More particularly, it relates to a socket having a gelatinous material encased between two thin, flexible plastic covers.

2. Description of the Prior Art

U.S. Pat. No. 5,258,037 to Caspers discloses a prosthetic liner formed of a gelatinous material. It is well-known that a patient using the gelatinous liner must apply large amounts of lotion to the residual limb before using the gelatinous liner because the material is very sticky. Moreover, the gel absorbs body oils and after a few weeks of use it emits strong, disagreeable odors. Still, the gel provides an excellent cushioning effect and thus is widely used by leg amputees.

What is needed, then, is a cushioned prosthetic socket that does not require a user to apply lotions and which does not emit unpleasant odors.

For the past twenty years or so, the leading prosthetic socket has been a socket made of flexible plastic of predetermined thickness. The socket has flexibility due to its plastic construction, but it is not padded and thus does not provide the comfort of the Caspers liner. However, since it is formed of plastic, it is not subject to the limitations of a gelatinous liner.

There is a need, then, for a socket that provides the cleanliness and odor-free service of a conventional plastic flexible socket, but which provides the comfort of a gelatinous liner.

It is also well-known among prosthetists that suction suspension is far superior to any type of mechanical suspension. A drawback to suction suspension arises from the fact that a standard socket, whether flexible or rigid, has a fixed, constant volume. The volume of a residual limb, however, changes during the lifetime of the prosthesis. Prior art attempts to compensate for this volume variation have included the use of silicone liners and inflatable bladders. Silicone liners add considerable weight to the prosthesis, and inflatable bladders require a pump. Moreover, the bladders are easily over-inflated by patients; this can result in damage to the tissue of the residual limb.

Thus, there is a need for an improved volume-adjustment bladder that cannot be over-inflated by the user thereof.

A prosthetic device may be designed for use in above-the-knee, below-the-knee, above-the-elbow, below-the-elbow, and disarticulation (through a joint) applications. The needed improvements in the art should be adaptable to all of such applications, without limitation.

However, in view of the art considered as a whole at the time the present invention was made, it was not obvious to those of ordinary skill in this art how the needed improvements could be provided.

SUMMARY OF THE INVENTION

The long-standing but heretofore unfulfilled need for an apparatus that overcomes the limitations of the prior art is now met by a new, useful, and nonobvious invention.

From the outset, it should be understood that the disclosure made herein refers, for convenience purposes, to a prosthetic socket having utility in above-the-knee applications. It would overly lengthen this disclosure to repeat the disclosure for below-the-knee, disarticulation, and other applications. However, from the description of an above-the-knee prosthetic socket provided herein, a prosthetist of ordinary skill will be able to make and use the novel socket in any prosthetic application. Thus, the specific locations of gelatinous material and the relative thicknesses at such locations as disclosed herein are intended for use in above-the-knee applications, and it will be apparent to those skilled in the art how to adapt the location of the gel, the shape of the gel, the amount of gel to be used, its thicknesses at varying locations, and so on, for other applications; all of such parameters are empirical matters in view of the disclosure made herein.

The present invention includes a socket having a thin, flexible inner cover made of a plastic material, a thin, flexible outer cover made of a plastic material, and a gelatinous material disposed between the inner and outer covers. This novel arrangement of parts harnesses the comfort provided by the gel and the cleanliness and odor-free characteristics of a conventional flexible plastic socket, without the disadvantages of each.

Since the socket that is disclosed for convenience purposes as aforesaid is used in above-the-knee applications, the gelatinous material is thick in preselected regions of a brim of the socket and tapers down in thickness to a featheredge at preselected regions where the gelatinous material ends. The inner and outer covers are secured to one another at their respective brims, and the inner and outer covers are adapted to be secured to a prosthetic frame so that the covers protect a residual limb from the gelatinous material and so that the gelatinous material provides a beneficial cushioning effect for the residual limb.

The gelatinous material may also be provided at a distal end of the socket in sandwiched relation between the inner and outer covers to provide a cushioning effect for a distal end of the residual limb.

The gelatinous material may be thin or discontinuous in a preselected region between the brim of the socket and the lowermost or distal end of the socket. The thin or discontinuous region, if present, divides the gelatinous material into an upper part and a lower part. The upper part of the gelatinous material has a featheredge formed at a terminus thereof so that the tapering down in thickness of the gelatinous material is substantially not felt by a user of the socket. The lower part has a featheredge as well.

At least one self-inflating volume-adjusting bladder means may be positioned in a preselected location to enhance a fit of the socket to a residual limb. The at least one bladder means is preferably provided in the form of a foam pad having air evacuated from its interstitial spaces prior to its positioning into the preselected location. The foam pad may be unenclosed or housed in a pouch.

When unenclosed or housed in a pouch, a means for introducing air into the interstitial spaces of the foam pad may include a manually-operated valve means that admits air into said interstitial spaces to inflate the pad in the absence of a mechanical pump means.

When housed in a pouch, one or more openings may be formed in the pouch so that air is always free to flow into or out of the interstitial spaces as the volume of the residual limb changes. Thus, as the residual limb increases in volume, air is driven out of the pad means through said openings and air automatically returns to the interstitial spaces of the pad means when the residual limb decreases in volume. No valve means is required when such openings are provided, said openings serving as a normally open valve means.

The novel self-inflating volume-adjusting bladder means may be positioned at any location between the novel inner and outer plastic covers that house the gelatinous material. It may also be positioned at any location between the novel outer cover and a conventional flexible or rigid prosthetic frame. Furthermore, the bladder means may be positioned at any location between a conventional flexible plastic inner socket and a conventional flexible or rigid prosthetic frame. When in any of said three positions, the bladder means may be provided in the form of an unhoused foam pad, of a foam pad housed in a pouch having a normally closed momentary valve, or of a foam pad housed in a pouch having a normally open valve in the form of one or more openings formed in the pouch. Thus, there are many combinations of the novel self-inflating volume-adjusting bladder means disclosed herein.

Since the novel bladder means of this invention is self-inflating, it has a predetermined maximum volume when fully inflated so that it cannot be over-inflated. Moreover, when the normally closed valve means is used, the bladder means is inflatable to a plurality of differing volumes dependent upon the length of time the valve means is opened.

It is a primary object of this invention to combine the respective benefits of cushioned, gelatinous liners and uncushioned flexible plastic sockets.

Another major object is to achieve said benefits without incurring the respective detriments of gelatinous liners and flexible plastic sockets.

A more specific object is to provide a socket having a gelatinous cushion that does not stick to a user's skin.

Another object is to provide a socket that does not absorb body oils.

Another object is to provide a self-inflating volume adjustment bladder means that cannot be over-inflated.

These and other important objects, features, and advantages of the invention will become apparent as this description proceeds.

The invention accordingly comprises the features of construction, combination of elements and arrangement of parts that will be exemplified in the construction hereinafter set forth, and the scope of the invention will be indicated in the claims.

BRIEF DESCRIPTION OF THE DRAWINGS

For a fuller understanding of the nature and objects of the invention, reference should be made to the following detailed description, taken in connection with the accompanying drawings, in which:

FIG. 1A is a partially sectional side elevational view of a prosthetic frame and socket of the prior art;

FIG. 1B is a partially sectional side elevational view of a prosthetic frame, socket, and liner of the prior art, with the liner being depicted in exploded relation to the frame and socket;

FIG. 2 is an exploded sectional view of the novel socket;

FIG. 3 is a sectional view of the novel socket when in its assembled configuration and ready for use;

FIG. 4 is a sectional view depicting the novel volume-adjusting bladder means when positioned between a conventional frame and the outer cover of the novel socket;

FIG. 5 is a sectional view depicting the novel volume-adjusting bladder means when used with the prior art frame and socket of FIG. 1A;

FIG. 6A is a sectional view of a self-inflating foam pad housed in a plastic pouch equipped with a normally closed momentary valve means;

FIG. 6B is a sectional view of a self-inflating foam pad housed in a plastic pouch having plural openings formed therein which serve as a normally open valve means; and FIG. 6C is a sectional view of a self-inflating foam pad when unhoused.

DETAILED DESCRIPTION OF THE PREFERRED EMBODIMENT

Referring first to FIG. 1A, it will there be seen that an above knee prosthesis of the prior art is denoted 11 as a whole. It includes a prosthetic foot 15, a pylon 21, a knee unit 23, a frame 25, an inner socket 27, and a suction socket valve 29.

FIG. 1B depicts the same prosthesis when improved by the addition of the gelatinous liner, denoted 31, of the prior art. This is the liner that absorbs body oils and which eventually becomes unsuitable for use as a result of such absorption.

Referring now to FIGS. 2 and 3, it will there be seen that an exemplary embodiment of the invention is denoted as a whole by the reference numeral 10.

Novel socket 10 includes a first or inner cover 12, a second or outer cover 14, gelatinous material 16 that surrounds inner cover 12, gelatinous material 18 that underlies inner cover 12, if used, an expandable foam pad 20, and a normally closed, momentary valve 22 including a push button 23. When used, novel socket 10 replaces inner socket 27 of the prior art.

In this particular embodiment, pad means 20 is unhoused, i.e., it is not enclosed or encased in a plastic pouch; it is the same pad means that is depicted again in FIG. 6C for convenience and explanatory purposes.

Inner cover 12 is formed of a thin, flexible plastic; it abuts the skin when liner 10 is worn and thus shields the skin from gelatinous material 16, 18. Outer cover 14 is also formed of a thin, flexible plastic and prevents the gelatinous material 16, 18 from contacting a conventional prosthetic frame 25.

Inner cover 12 has an annular brim that circumscribes the annular brim of prosthetic frame 25. The anterior part thereof is denoted 24 and has a general hook shape. The posterior part thereof is denoted 26 and is also generally hook-shaped. Whereas anterior part 24 has a substantially vertical axis of symmetry when frame 25 is in an upright disposition, posterior part 26 has an almost horizontal axis of symmetry when said frame is in said disposition. Of course, the precise orientation and shape of the anterior part 24 of the brim and posterior part 26 of said brim will vary from patient to patient because different patients will be fitted with different sockets. Moreover, as already mentioned, sockets for applications other than above-the-knee amputations will incorporate the teachings and suggestions of this disclosure into the context of such other applications.

It is an important teaching of this invention, for above-the-knee applications, that gelatinous material 16, which may or may not completely encircle inner cover 12, depending upon the particular requirements of patients, must be at its thickest in the brim area of the socket. This is where a significant part of the patient's weight must be supported. However, little or no padding may be required in the lateral area thereof. In other applications, the placement, shape, size, thickness, and other characteristics of the gel are adapted as needed.

Note that gelatinous material 16 tapers downwardly to a featheredge 17 at its terminus, whether said terminus be at its lowermost part or some other location. Less cushioning, or even no cushioning, may be needed along the vertical sides of the residual limb, depending upon the patient and the application. In all applications, the gradual diminution in gel thickness as the terminus of the gel is approached ensures that the wearer will not feel any abrupt discontinuation of gel.

Gelatinous material 18, if used, absorbs shocks encountered by the residual limb when the amputee is walking because it is positioned directly below said residual limb as should be clear from FIG. 3.

Since the lowermost sides of the residual limb (in an above-the-knee application) require virtually no support or cushioning, the gelatinous material may be discontinuous in the annular area denoted 30 in FIG. 3, thereby dividing said gelatinous material into upper part 16 and lower part 18. Note that gelatinous material 18 has an annular featheredge 19 at its uppermost edge so that the amputee will be unable to feel where gelatinous material 16 ends and where gelatinous material 18 begins.

It is important to note, however, that gelatinous material 16 and gelatinous material 18 may also be integrally formed with one another, i.e., discontinuity 30 is not required. Since little or no cushioning is needed in said area 30, or in the lateral area as mentioned above, it saves materials to eliminate said gelatinous material in regions where it is not needed. However, an integrally formed socket having a relatively thin extent of gelatinous material extending between the upper part 16 and lower part 18 of gelatinous material is within the scope of this invention.

Unpadded annular region 30 may be put to further advantageous use, at the option of the prosthetist, by positioning expandable foam pad 20 in such region, i.e., between inner and outer covers 12 and 14 as depicted in FIG. 3. The pad in FIG. 3 is unhoused because inner and outer covers 12 and 14 serve as a pouch, for all practical purposes.

As depicted in FIG. 4, novel self-inflating volume-adjusting bladder means 20 may also be positioned outside outer cover 14. In the embodiment of FIG. 4, the foam pad is housed in a plastic pouch and is positioned between a conventional frame 25 and outer cover 14 of the novel socket. Air valve 22 having momentary push button 23 admits air into the foam pad when depressed by the user, but, as in all other embodiments, even if the user depresses the push button for a very extended period of time, the volume of pad 20 will not exceed a safe volume as predetermined by the prosthetist.

FIG. 5 depicts yet another possible use of the novel self-inflating volume-adjusting bladder means 20 in connection with a prior art prosthesis. In this embodiment, foam pad 20, housed within a pouch, is positioned between a prior art frame 25 and a prior art inner socket 27 which is formed of a flexible plastic.

FIG. 6A depicts foam pad 20 within a plastic pouch 20a and valve means 22. FIG. 6B depicts foam pad 20 within a plastic pouch 20a with plural openings 20b formed therein which serve as normally open valve means, and FIG. 6C depicts a foam pad 20 when unhoused, as in FIGS. 2 and 3. It should be understood that the pad means of FIGS. 3 (pad between novel inner and outer covers 12 and 14), FIG. 4 (pad between novel outer cover 14 and conventional frame 25) and FIG. 5 (pad between conventional frame 25 and conventional flexible plastic inner socket 27) may be the pad means of FIGS. 6A–6C, respectively. In other words, each pad means of FIGS. 6A–6C may be employed in the embodiment of FIG. 3, in the embodiment of FIG. 4, and in the embodiment of FIG. 5.

The plurality of openings 20b (FIG. 6B) formed in pouch 20a admit air into the interstitial spaces 20c of the foam at all times so that the pad means expands to its maximum volume when in repose, reduces in volume as the volume of the residual limb increases, and automatically increases in volume as the residual limb decreases in volume, all without the user being required to manipulate a valve means.

Pad 20 may also be positioned so that it intrudes into a gel-cushioned region as well, i.e., there is no requirement that the pad be positioned entirely in an uncushioned region. Moreover, more than one foam pad might be called for in appropriate cases. Furthermore, the annular or circumferential extent, as well as the vertical extent and thickness and other parameters of the foam pad may vary as well, it being understood that the depicted examples are merely exemplary. The pad is not necessarily of foam construction.

Outer cover 12 and inner cover 14 are secured to one another at their respective brims, i.e., in the region denoted 13 in FIG. 3. The attachment may be made by any suitable means such as the use of a suitable glue, or the gelatinous material itself may be used as an adhesive. Moreover, covers 12 and 14 can be heat-sealed together, i.e., melted and allowed to cool so that they merge together.

The thin, flexible plastic that forms inner and outer covers 12 and 14 may be any suitable plastic material that is impervious to gelatinous material 16, 18. It must also be suitable for prolonged contact with human skin. Numerous plastics fill these requirements, as will be apparent to those skilled in the art of materials. The covers eliminate the need for the patient to apply lotions to the residual limb and since the gelatinous material does not contact the skin, no body oils are absorbed by it and no odors are produced. Thus, amputees gain the benefits of a socket cushioned by a gel liner without the detriments associated with a liner made of such gel and without the detriments associated with a conventional uncushioned flexible plastic socket. The padding is the thickest where it is most needed, and provides a level of comfort heretofore unknown.

It will thus be seen that the objects set forth above, and those made apparent from the foregoing description, are efficiently attained and since certain changes may be made in the foregoing construction without departing from the scope of the invention, it is intended that all matters contained in the foregoing construction or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described,

What is claimed is:

1. A socket adapted to fit within a prosthetic frame, comprising:

a thin, flexible inner cover made of a plastic material;

said inner cover having a brim means adapted to circumscribe a brim means of said prosthetic frame;

a thin, flexible outer cover made of a plastic material;

said outer cover having a brim means;

a gelatinous material disposed between said inner and outer covers;

said gelatinous material being thick in preselected regions of said socket and tapering down in thickness to a featheredge at preselected regions where said gelatinous material ends;

said inner and outer covers being secured to one another at their respective brim means so that said gelatinous material is sandwiched therebetween; and said inner and outer covers being adapted to be secured to said prosthetic frame;

whereby said inner and outer covers are adapted to protect a residual limb from said gelatinous material; and whereby said gelatinous material provides a beneficial cushioning effect for the residual limb.

2. The socket of claim 1, wherein said gelatinous material is also provided at a distal end of said socket in sandwiched relation between said inner and outer covers to provide a cushioning effect for a distal end of the residual limb.

3. The socket of claim 2, wherein said gelatinous material is discontinuous in a preselected region between said respective brim means of said inner and outer covers and said distal end of said socket, said discontinuity dividing said gelatinous material into an upper part and a lower part.

4. The socket of claim 3, wherein said upper part of said gelatinous material has a featheredge formed at a terminus thereof so that said tapering down in thickness of said gelatinous material is substantially not felt by a user of said socket.

5. The socket of claim 1, further comprising at least one self-inflating volume-adjusting bladder means positioned in a preselected region between said inner cover and said outer cover.

6. The socket of claim 5, wherein said bladder means is a foam pad having air evacuated from interstitial spaces thereof prior to positioning of said foam pad in said preselected region.

7. The socket of claim 6, wherein said foam pad is housed in a pouch.

8. The socket of claim 7, further comprising a plurality of openings formed in said pouch so that said foam pad is in continuous fluid communication with ambient air.

9. The socket of claim 6, further comprising a normally closed valve means in fluid communication with said foam pad so that ambient air is admitted into said foam pad only when said normally closed valve means is open.

10. The socket of claim 1, further comprising:

at least one self-inflating volume-adjusting bladder means adapted to be positioned at a preselected location between said outer cover and said prosthetic frame.

11. The socket of claim 8, wherein said bladder means is a foam pad having air evacuated from interstitial spaces thereof prior to positioning of said foam pad in said preselected location.

12. The socket of claim 11, wherein said foam pad is housed in a pouch.

13. The socket of claim 12, further comprising a plurality of openings formed in said pouch so that said foam pad is in continuous fluid communication with ambient air.

14. The socket of claim 11, further comprising a normally closed valve means in fluid communication with said foam pad so that ambient air is admitted into said foam pad only when said normally closed valve means is open.

* * * * *